United States Patent [19]

Schimanski

[11] 3,964,684

[45] June 22, 1976

[54] DEODORIZING OR PERFUMING ASSEMBLY

[75] Inventor: Georg Schimanski, Hagen, Germany

[73] Assignee: Globol-Werk GmbH

[22] Filed: Oct. 15, 1975

[21] Appl. No.: 622,462

[30] Foreign Application Priority Data
Apr. 21, 1975 Germany.................................. 281

[52] U.S. Cl.................................... 239/56; 239/57
[51] Int. Cl.².......................................... A61L 9/04
[58] Field of Search.................... 239/34, 36, 53–60; 43/132 R; 161/406

[56] References Cited
UNITED STATES PATENTS

| 406,076 | 7/1889 | Allen | 239/55 |
| 1,742,962 | 1/1930 | McCrosky | 239/55 |
| 1,841,889 | 1/1932 | Grunwald | 239/56 |
| 2,351,267 | 6/1944 | Irwin | 239/57 |
| 2,615,754 | 10/1952 | Lindenberg | 239/36 |
| 3,807,082 | 4/1974 | Hautmann et al. | 239/55 X |

Primary Examiner—Robert S. Ward, Jr.
Attorney, Agent, or Firm—Heinrich W. Herzfeld; Gilbert L. Wells

[57] ABSTRACT

A deodorizing or perfuming assembly having a casing consisting of a mantle having two open ends and two flattened side walls opposite one another. An attachment for affixing the assembly to a supporting surface is located on one of the flattened side walls and this side wall has slots for the access of air to the interior of the mantle. A plate or sheet of absorbent material impregnated with a deodorizing or perfuming substance is located in the interior of the mantle. A clamp protruding from one of the interior faces of the flattened side walls holds the plate or sheet with its surface spaced from the inside wall surface of the mantle.

11 Claims, 10 Drawing Figures

Fig. 4a
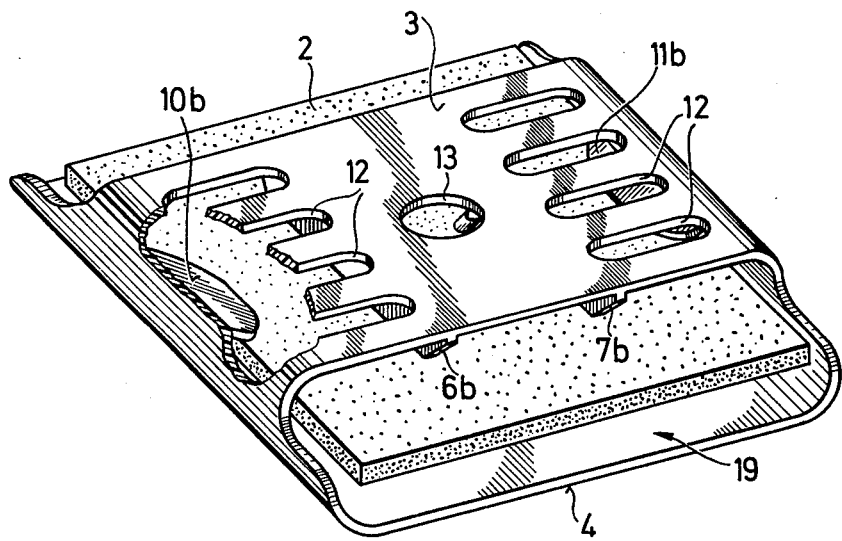
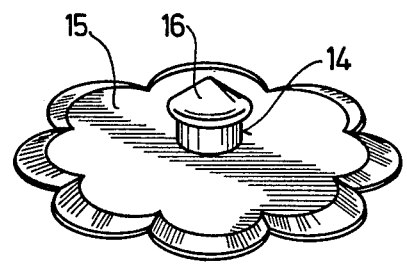
Fig. 4b

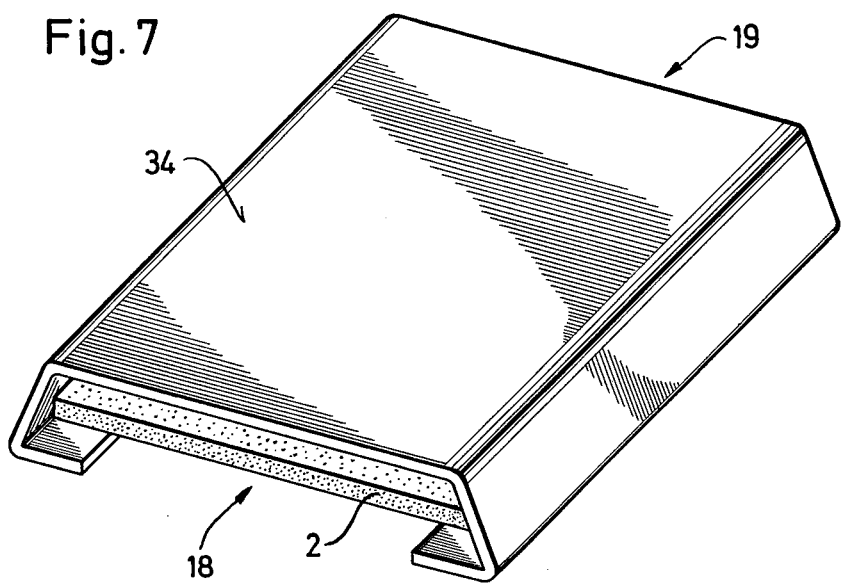
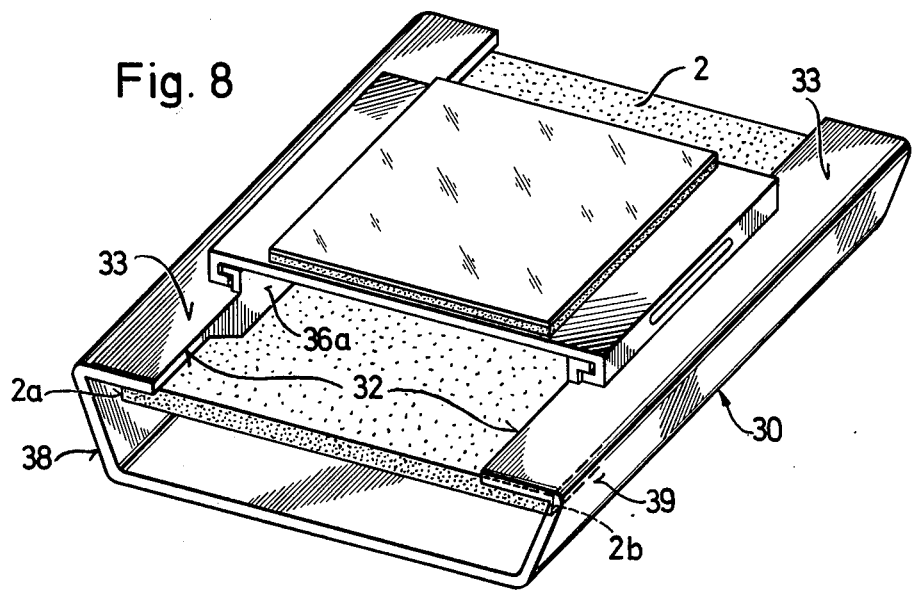

DEODORIZING OR PERFUMING ASSEMBLY

This invention relates to a deodorizing or perfuming assembly comprising a casing having at least one opening and a mass of absorbent material inside said casing and being impregnated with a deodorizing or perfuming substance. The invention relates further to a casing and carrier assembly the carrier of which is adapted for absorbing a deodorizing or perfuming substance. Finally, the invention relates to a casing having several openings and being adapted for receiving and firmly holding therein a carrier being adapted for absorbing or having absorbed therein a deodorizing or perfuming substance.

Assemblies of the first-mentioned type which contain a mass of absorbent material having absorbed therein a perfume, which mass is sealed in an openable envelope including a front sheet heat-sealed to a back sheet and which comprise means for adhesively attaching the envelope to a surface, for instance a floor, a shelf, a cabinet, a garbage pail, a toilet bowl rim or other structure that emits unpleasant odors have been described in U.S. Pat. No. 3,575,345 granted to Fred H. Buck, Jr. on Apr. 20, 1971. It is an advantage of this known deodorizing structure that it can be easily installed without physically handling the product itself. However, this known device has the drawback that only a narrow end strip of the envelope can be torn off to expose only a relatively small fraction of the perfume impregnated mass to the ambient air while the major portion of the surface of the perfumed mass remains tightly sealed in the envelope.

While this retards evaporation and lengthens the time of usefulness it also means a waste of expensive perfume which will be retained in the mass. Moreover, the evaporation surface is relatively small compared with the volume of the reservoir constituted by the absorbent mass, and the perfume used must therefore have adequately high volatility and rate of diffusion.

It is an object of the instant invention to provide a deodorizing or perfuming assembly of the initially described type which, while possessing the advantage of the known device of being easily installable without physically handling the product itself, has the major portion of the surface of the absorbent carrier exposed to the ambient air during use and is therefore suitable for being impregnated with perfumes, deodorants and the like active substances having a wide range of volatility and moderate to small diffusion rates.

It is another object of the invention to provide a casing and carrier assembly in which the carrier is easily accesible and which assembly can be easily mounted, without physical contact with the carrier, in particular on the inside of the lid of a garbage pail.

It is yet another object of the invention to provide a casing and carrier assembly comprising means for detachably affixing the assembly to the inside of a garbage pail or a toilet bowl or the like structure.

These objects are attained in accordance with the invention by providing an assembly of the initially described type wherein the casing consists of a mantle having two open ends and two flattened side walls opposite one another, and comprises means for affixing the assembly to a supporting surface which means are attached to one of the said flattened side walls, and the latter flattened side wall being provided with a slot or slots for the access of air therethrough to the interior of the mantle, and clamping means protruding from the interior faces of the aforesaid flattened side walls, located opposite one another for clampingly engaging the said carrier; and wherein said carrier is a plaque or sheet of absorbent material, held fast by the clamping means.

The connecting wall portions of the mantle intermediate the opposite flattened side walls are preferably curved but can also be flat and joined to the flattened side walls at an angle, e.g. a right angle or an oblique angle. In the latter case, the cross section of the mantle is of trapezoid shape, in the former case it is rectangular.

The flattened side wall bearing the affixing means can have a single longitudinal slot, with the affixing means engaging angular fastening means on both sides of the slot. Preferably, however, the affixing means have a protrusion or thorn which penetrates into a central aperture in the flattened side wall of the mantle, and a plurality of air-venting slots are provided in the same flattened side wall on both sides of the aforesaid aperture. These slots can extend beyond the edge of the flattened side wall into the intermediate rounded wall portions. The mantle is preferably made of a synthetic plastic material such as polyethylene.

The affixing means preferably comprise an adhesive layer by means of which they can be attached to a surface.

The carrier plaque, plate or sheet is preferably made of cardboard felt, paper felt, unsized paper or the like cellulosic absorbent material.

The deodorant or perfuming compositions used for impregnating the carrier are well known. Preferably, the assembly according to the invention is attached to the inside of a lid of a garbage pail. In this case, it has been found advantageous to impregnate the carrier plate with a solution consisting of 85.70 parts by weight of a perfume, preferably a perfume having a lemon odor, such as citronellal, 7.15 parts by weight of natural lemon oil and 7.15 parts by weight of diethyltoluamide. This composition is not only an excellent deodorant, but it is also an excellent repellent for insects in particular for domestic flies.

It is of particular advantage that the frontal flattened side wall of the assembly according to the invention has a closed surface. It has been found that assemblies having slots or other openings in their frontal wall showed a serious drawback when affixed to the inside of the lid of a garbage pail. When the pail was filled so much that the lid was pressed down on the garbage compressing the same during closure, garbage would clog the openings in the frontal wall of the deodorizing or perfuming assembly and parts of garbage would stick to the same when the lid was opened.

The invention is further illustrated, by way of example only, in the accompanying drawing, in which FIG. 1 shows a preferred embodiment of the assembly according to the invention in a frontal perspective view;

FIG. 4a is a rear view in perspective of the main parts of the preferred embodiment; and FIG. 4b is a perspective view of a fixing member of the embodiment separated from the main parts thereof;

FIG. 7 is a perspective frontal view of a third embodiment of the assembly according to the invention; and FIG. 8 is a rear view in perspective thereof.

Figure 1:
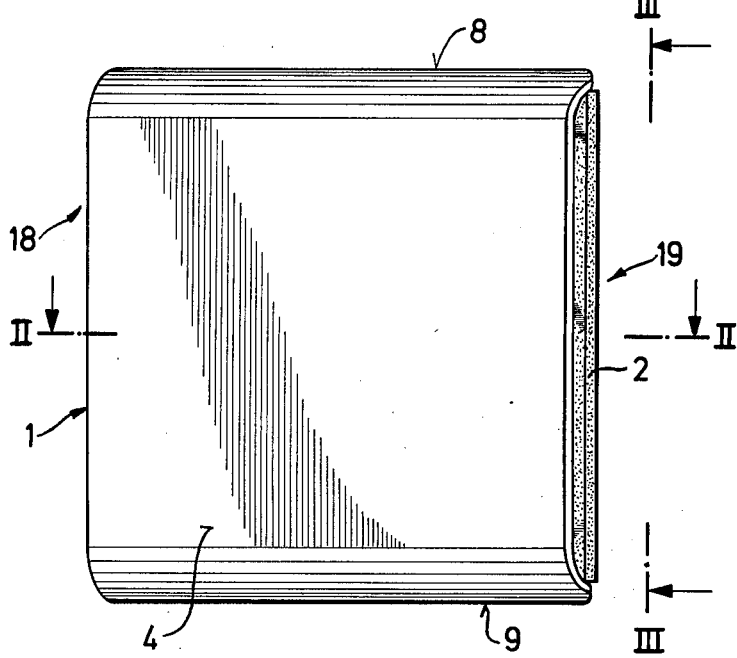
Figure 3:
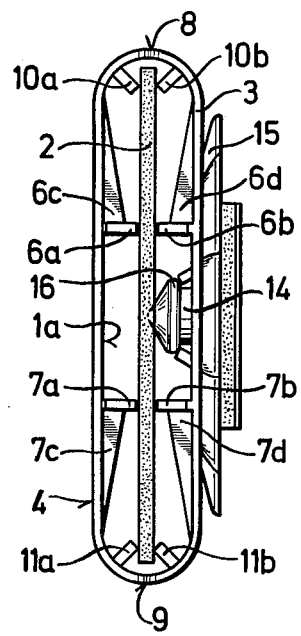
FIG. 3 is a side view of the embodiment shown in FIG. 1 as indicated by arrow III.
Figure 2:
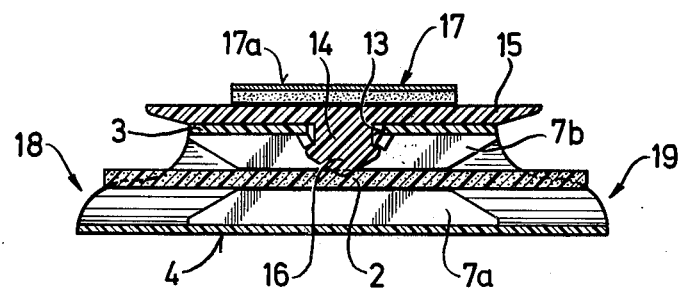
FIG. 2 is a cross-sectional view of the embodiment shown in FIG. 1 in a plane indicated by II—II therein.

The embodiment shown in FIGS. 1 to 4 ( a and b ) comprises a casing in the form of a closed-upon-itself mantle 1 of a cross section constituting a flattened ellipse as shown in FIG. 3. In the mantle 1 there is inserted a rectangular plate 2 of absorbent material serving as the carrier, which protrudes from the narrowed rear wall 3 of mantle 1 while it is completely covered by the closed front wall 4 thereof.

Carrier plate 2 is held spaced from the interior wall 1a of mantle 1 by pairs of holding members 6a, 6b, and 7a, 7b which protrude from the interior wall 1a, being preferably integral therewith, the two members of each pair protruding one from the inside of the front wall 4 and the other from the inside of the rear wall 3, and leaving a gap therebetween slightly narrower than the thickness of plate 2, so that when plate 2 is inserted into the gap it is securely and clampingly held therein.

Holding or clamping members 6a, 6b and 7a, 7b preferably extend in the form of ridges across the interior wall 1a at the inside of front wall 4, parallel to the closed rounded side walls 8 and 9 of mantle 1.

Preferably, the foot portions of ridges 6a, 6b and 7a, 7b are stiffened against bending by transverse prop members 6c, 6d and 7c, 7d of triangular cross section, which are preferably molded integrally with the mantle and the ridges therein.

Similar pairs of clamping ridges protrude from the inside of the curved side walls 8 and 9 whereof members 10a and 11a extend across the inside for approximately the length of plate 2, while opposite ridges 10b and 11b are shorter than the reduced-diameter rear wall 3.

These ridges project preferably perpendicularly from the inside of curved side walls 8 and 9 and therefore extend at an inclined angle into contact with plate 2.

The rear wall 3 is provided with a plurality of vents in the form of elongated openings 12 and in the center of rear wall 3 there is an aperture 13 into which the male portion 14 of an affixing member 15 can be detachably inserted, but the respective diameters of aperture 13 and male portion 14 are so dimensioned that mantle 1 is held firmly on affixing member 15. Male member 14 is preferably provided with an enlarged head portion 16 to hold mantle 1 more securely on affixing member 15.

As mantle 1 is open at both ends 18 and 19 and elongated vents 12 are provided in rear wall 3, and as plate 2 is held with almost its entire surface away from interior mantle wall 1a, optimal conditions are provided for the evaporation of deodorants, perfumes and insect repellents from plate 2 and the distribution of the vapours thereof in the surrounding space, for instance in the interior of a garbage pail.

Figure 5:
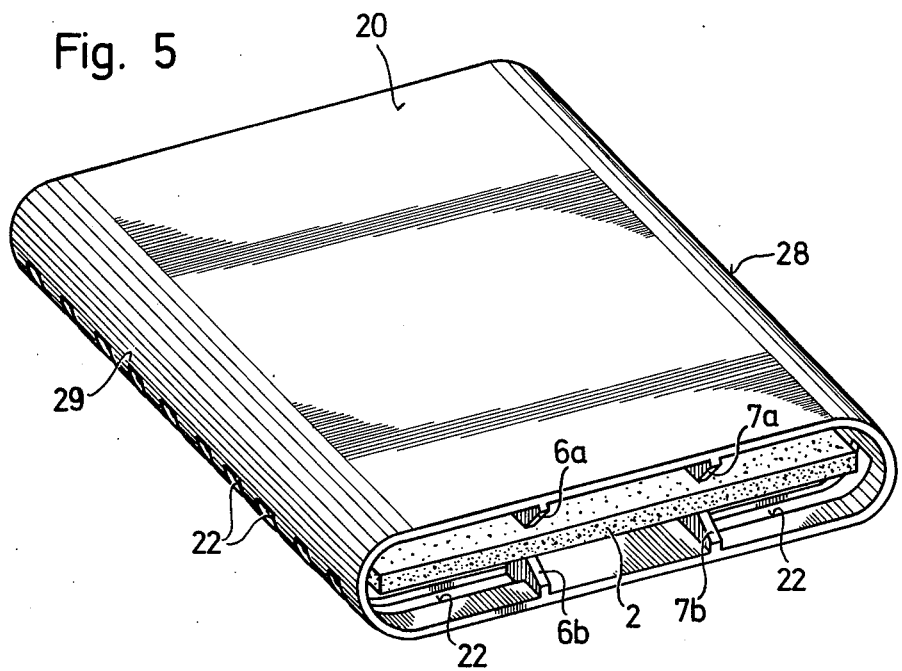
FIG. 5 shows in perspective frontal view another embodiment of the assembly according to the invention.
Figure 6:
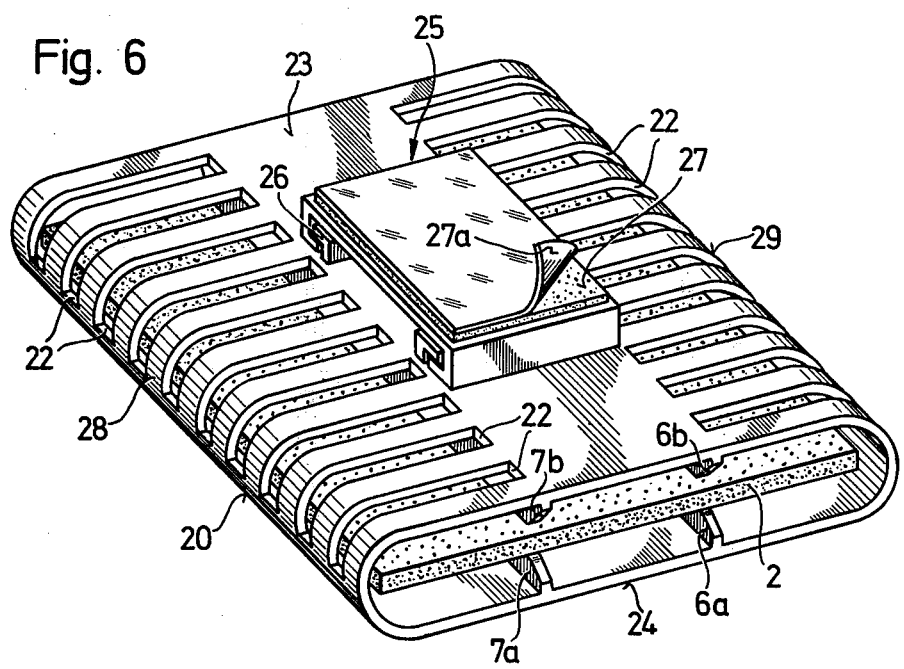
FIG. 6 is a rear view in perspective thereof.

In the embodiment of FIGS. 5 and 6, carrier plate 2 is fastened in the mantle 20 in the same manner as in the preceding embodiment. However, the vents in the rear wall 23 which, in this case, is of the same size and configuration as the front wall 24, are in the form of elongated slots 22 extending into the curved side walls 28 and 29 of mantle 20.

Affixing member 25 is held on rear wall 23 by clamping prongs 26 which are preferably molded integral with rear wall 23. The flat bottom faces 17 in the first embodiment and 27 in the second embodiment of affixing members 15 and 25, respectively, are provided as adhesive surfaces which are protected before use by a peelable protecting foil 17a, 27a.

In the embodiment shown in FIGS. 7 and 8, mantle 30 which has a closed front wall 34 and is open at two ends 18 and 19 is of trapezoidal cross-sectional configuration.

The elongated vents in the rear wall 33 of mantle 30 are replaced by a single slot 32 extending from open end 18 to open end 19. Rear wall 33 extends at the larger base of the trapezoidal and frontal face 34 at the narrower top thereof. Consequently, a single pair of clamping ridges projecting from the rim of slot 32 inwardly, and of which only one ridge 36a is visible in FIG. 8, is required for holding rigid plate 2 firmly in position in mantle 30, because side rims 2a and 2b of plate 2 rest on the convergent slopes of side walls 38 and 39 of mantle 30.

Figure 9:
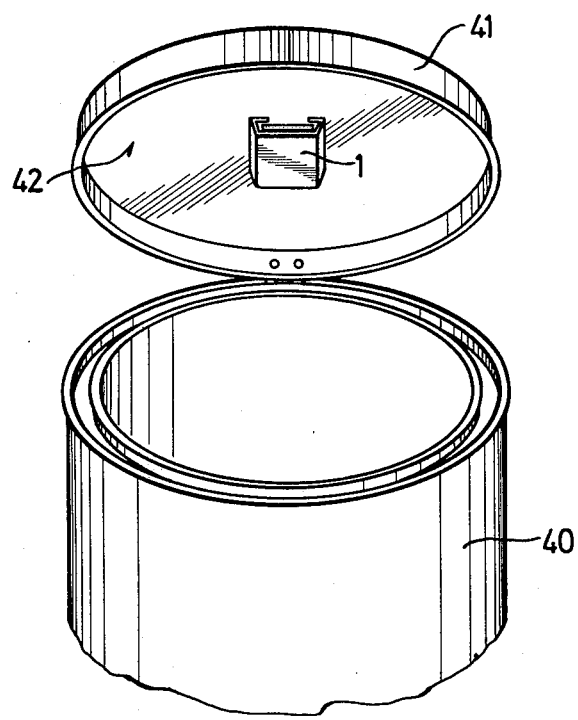
FIG. 9 shows the attachment of an assembly according to the invention to the inside of the lid of a garbage pail.

FIG. 9 shows the upper part of a garbage pail 40 having a lid 41 in half open position. An assembly according to the invention as illustrated in FIGS. 1 to 4 is attached to the inside 42 of lid 41.

I claim:

1. A deodorizing or perfuming assembly comprising a casing consisting of a mantle having two open ends and two flattened side walls opposite one another.
   means for affixing the assembly to a supporting surface which means are attached to one of the said flattened side walls and which latter flattened side wall has provided a slot or slots for the access of air therethrough to the interior of said mantle,
   a plate or sheet of absorbent material being impregnated with a deodorizing or perfuming substance free from or having an insect repellent adjuvant, said sheet or plate being located in the interior of said mantle, and
   clamping means protruding at least from one of the interior faces of said flattened side walls, and being adapted for clampingly engaging said plate or sheet, to hold the latter fast with its surface spaced from the inside wall surface of said mantle.

2. An assembly as described in claim 1, wherein said mantle comprises connecting wall portions intermediate its opposite flattened side walls, said connecting wall portions being curved.

3. An assembly as described in claim 1, wherein said mantle comprises connecting wall portions intermediate its opposite flattened side walls, said connecting wall portions being flat and joined to said flattened side walls at an oblique angle whereby said mantle has a trapezoid cross section.

4. An assembly as described in claim 3, wherein said flattened side wall bearing said affixing means has a single longitudinal slot and angular fastening means on both sides of said slot which fastening means are engaged by said affixing means.

5. An assembly as described in claim 2, wherein one of said flattened side walls is closed and constitutes the frontal wall of said assembly and the other flattened side wall has an aperture,
   and said affixing means comprise a protrusion adapted for penetrating into said aperture.

6. An assembly as described in claim 5, wherein said flattened side wall having said aperture also has a plurality of air-venting slots.

7. An assembly as described in claim 6, wherein said aperture is in the center of the flattened side wall and said slots extend toward or into said curved connecting wall portions.

8. An assembly as described in claim 1, wherein said mantle is of synthetic plastic material.

9. An assembly as described in claim 1, wherein said plate or sheet is of an absorbent cellulosic material.

10. An assembly as described in claim 1, wherein said fixing means comprise an adhesive layer by means of which they can be stuck onto a surface.

11. An assembly as described in claim 4, wherein said flattened side wall bearing said affixing means is the larger and said opposite flattened side wall is the smaller wall in said mantle of trapezoid cross section, and wherein said plate or sheet has a surface area of a size intermediate the surface areas at the inner side of said flattened side walls, whereby said plate or sheet comes to rest on the inclined flat connecting wall portions, and said clamping means protruding from the inside face of said larger flattened side wall and holding said plate or sheet firmly in position against said connecting wall portions are spaced from the inner faces of both said flattened side walls.

* * * * *